(12) United States Patent
Fabula et al.

(10) Patent No.: US 8,476,601 B1
(45) Date of Patent: Jul. 2, 2013

(54) IDENTIFYING AN ATOMIC ELEMENT USING AN INTEGRATED CIRCUIT

(75) Inventors: Joseph J. Fabula, Tucson, AZ (US); Austin H. Lesea, Los Gatos, CA (US); Raymond J. Matteis, Aptos, CA (US)

(73) Assignee: Xilinx, Inc., San Jose, CA (US)

( * ) Notice: Subject to any disclaimer, the term of this patent is extended or adjusted under 35 U.S.C. 154(b) by 1349 days.

(21) Appl. No.: 12/004,968

(22) Filed: Dec. 20, 2007

(51) Int. Cl.
*G01N 23/00* (2006.01)

(52) U.S. Cl.
USPC .................................... 250/390.04

(58) Field of Classification Search
USPC .................................... 250/390.04
See application file for complete search history.

(56) References Cited

U.S. PATENT DOCUMENTS

| | | | |
|---|---|---|---|
| 2,912,302 A * | 11/1959 | Connick et al. | 423/12 |
| 3,439,168 A * | 4/1969 | Lindsley | 250/303 |
| 4,378,498 A * | 3/1983 | Givens | 250/252.1 |
| 4,529,884 A * | 7/1985 | Wolicki et al. | 250/370.07 |
| 5,241,569 A * | 8/1993 | Fleming | 376/159 |
| 6,577,697 B2 * | 6/2003 | Pearcy et al. | 376/159 |
| 2004/0212388 A1 * | 10/2004 | Baumann | 324/765 |

OTHER PUBLICATIONS

Lesea et al., "The Rosetta Experiment: Atmospheric Soft Error Rate Testing in Differing Technology FPGAs", IEEE Transactions of Device and Materials Reliability, vol. 5 No. 3, Sep. 2005, 317-328 pages.

* cited by examiner

*Primary Examiner* — David Porta
*Assistant Examiner* — Shun Lee
(74) *Attorney, Agent, or Firm* — LeRoy D. Maunu

(57) ABSTRACT

Systems and methods are provided for identifying an atomic element in proximity to an integrated circuit. Trace amounts of a contaminant are identifiable. The atomic element is exposed to neutron radiation to convert a portion of the atomic element into a radioactive isotope of the atomic element. Upsets are measured for the binary states of the memory cells of the integrated circuit during a time period following the exposure to the neutron radiation. The atomic element is identified from the upsets of the binary states of the memory cells of the integrated circuit.

20 Claims, 3 Drawing Sheets

IDENTIFYING AN ATOMIC ELEMENT USING AN INTEGRATED CIRCUIT

FIELD OF THE INVENTION

The present invention generally relates to analyzing defects in an integrated circuit, and more particularly to identifying contaminants of an integrated circuit.

BACKGROUND

The fabrication of an integrated circuit is a complex and precise process. A contaminant may be introduced during the fabrication of an integrated circuit. The chemical supplies used to fabricate an integrated circuit may be contaminated or the equipment used to manufacture the integrated circuit may malfunction and contaminate the integrated circuit.

Very low levels of a contaminant may adversely affect the operation of the integrated circuit. For example, a few parts per billion of a radioactive contaminant may cause soft errors that make the operation of the integrated circuit unreliable.

It may be time consuming and expensive to identify a contaminant in an integrated circuit. The analysis may need to extract the contaminant from the integrated circuit and the extraction process may destroy the integrated circuit. The analysis may be especially difficult for very low levels of a contaminant.

The present invention may address one or more of the above issues.

SUMMARY

Various embodiments of the invention provide a system for identifying an atomic element. The atomic element is included in an integrated circuit having memory cells with a binary state. A neutron generator generates neutrons that convert a portion of the atomic element into a radioactive isotope of the atomic element. A byproduct from the radioactive decay of the radioactive isotope causes upsets of the binary states of the memory cells. An analyzer identifies the atomic element in response to the upsets of the binary states of the memory cells.

Various other embodiments of the invention provide a method for identifying an atomic element in proximity to an integrated circuit. The atomic element is exposed to neutron radiation to convert a portion of the atomic element into a radioactive isotope of the atomic element. Upsets are measured for the binary states of the memory cells of the integrated circuit during a time period following the exposure to the neutron radiation. The atomic element is identified from the upsets of the binary states of the memory cells of the integrated circuit.

It will be appreciated that various other embodiments are set forth in the Detailed Description and Claims which follow.

BRIEF DESCRIPTION OF THE DRAWINGS

Various aspects and advantages of the invention will become apparent upon review of the following detailed description and upon reference to the drawings, in which:

FIG. 1 is a block diagram of a system for identifying an atomic element in accordance with various embodiments of the invention;

FIG. 2 is a block diagram of a programmable logic device for identifying a contaminant within the programmable logic device in accordance with various embodiments of the invention; and FIG. 3 is a flow diagram of a process for identifying an atomic element in accordance with various embodiments of the invention.

DETAILED DESCRIPTION OF THE DRAWINGS

FIG. 1 is a block diagram of a system for identifying an atomic element 102 in accordance with various embodiments of the invention. The atomic element 102 might be a contaminant within the integrated circuit 104 that affects the operation or reliability of the integrated circuit 104. In one example, the atomic element 102 is a contaminating ion within a gate oxide that affects the threshold voltage and leakage current of transistors in the integrated circuit 104. The atomic element 106 might be contaminant nearby the integrated circuit 104 that affects the operation or reliability of the integrated circuit 104. In another example, the atomic element 106 is a radioactive heavy metal contaminating the solder connecting the integrated circuit 104 to a printed circuit board (not shown). Radioactive decay of the heavy metal generates alpha particles that cause soft errors during the operation of integrated circuit 104. Identifying the atomic element 102 or 106 helps identify the source of the contaminant of the integrated circuit 104. Various embodiments of the invention identify trace amounts of a contaminant in or nearby an integrated circuit. The remainder of this example is directed to an atomic element 102 within the integrated circuit 104. It will be clear to those of skill in the art that the system and process can also be used to identify an atomic element 106 nearby the integrated circuit 104.

A neutron generator 108 provides a means for generating neutron radiation for exposing the atomic element to the neutron radiation. In one embodiment, neutron generator 108 generates a beam of neutrons 110 and integrated circuit 104 is positioned within the beam of neutrons 110 to expose the atomic element 102 to the neutrons 110.

Some of the neutrons 110 are absorbed into the nucleus of the atomic element 102, converting the atomic element 102 into a radioactive isotope 112 of the atomic element. The atomic element 102 is converted into a radioactive isotope 112 of the atomic element after absorbing one or more of the neutrons 110. It will be appreciated that more than one isotope of the atomic element 102 can be created and both stable and radioactive isotopes can be created. The fraction of the atomic element 102 converted into the radioactive isotope 112 depends on the flux of the beam of neutrons 110, the duration of exposing the atomic element 102 to the beam of neutrons 110, and a cross-section of the atomic element 102 for absorbing the neutrons 110.

The radioactive isotope 112 decays into byproducts 114 and 116. Byproduct 116 may be an alpha particle, for example. The rate of production of byproduct 116 depends on the quantity of isotope 112 and the half-life for the radioactive decay of the isotope 112.

Byproduct 116 can affect integrated circuit 104. For example, byproduct 116 can generate a stream of hole and electron pairs while passing through the substrate of the integrated circuit 104. Depending upon the electric fields within the substrate, a circuit node of the integrated circuit 104 can capture the holes or the circuit node can capture the electrons. The total charge captured at the circuit node can be enough to change the binary value of the circuit node. For example, integrated circuit 104 includes memory cells 118, 120, and 122 storing respective binary states 124, 126, and 128, and byproduct 116 upsets the binary state 128 of memory cell 122.

Figure 1:
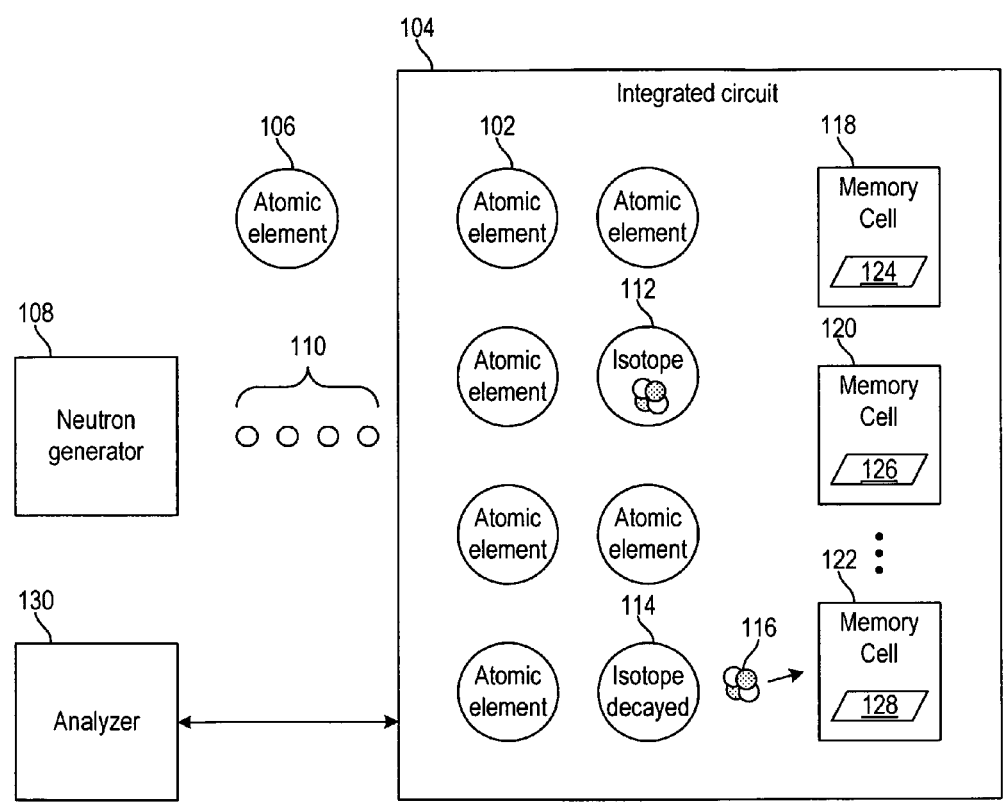

Analyzer 130 monitors the binary states 124, 126, and 128 of the memory cells 118, 120, and 122. Analyzer 130 provides a means for measuring upset of the memory cells and identifying the atomic element from these upsets.

In one embodiment, analyzer 130 performs a sequence of reads of the memory cells 118, 120, and 122 following the exposure of the integrated circuit 104 to the neutrons 110. For each read in the sequence, the analyzer 130 compares the binary states 124, 126, and 128 with expected values and records any binary state 128 that is upset. Analyzer 130 records the time of the read and a number of the binary states 124, 126, and 128 that are upset. The time of the read approximates the time of any upset detected by the read.

As the radioactive isotope 112 decays, the amount of radioactive isotope 112 decreases. The radioactive isotope 112 usually has an exponentially declining rate of radioactive decay. Generally, the half-life of the radioactive isotope 112 is the time interval for half of the radioactive isotope 112 to decay. As the amount of radioactive isotope 112 decreases, the rate of production of byproduct 116 and the rate of upsets of binary states 124, 126, and 128 decrease correspondingly. Thus, the decrease in the rate of upsets gives the decrease in the rate of radioactive decay of radioactive isotope 112. For example, the time interval for the upset rate to reduce by one-half is the half-life of the radioactive isotope 112.

Because the half-lives of radioactive isotopes are well known, the radioactive isotope 112 of the atomic element 102 or 106 is identifiable from the half-life of the radioactive isotope 112. Identifying the radioactive isotope 112 also identifies the atomic element 102 or 106.

Figure 2:
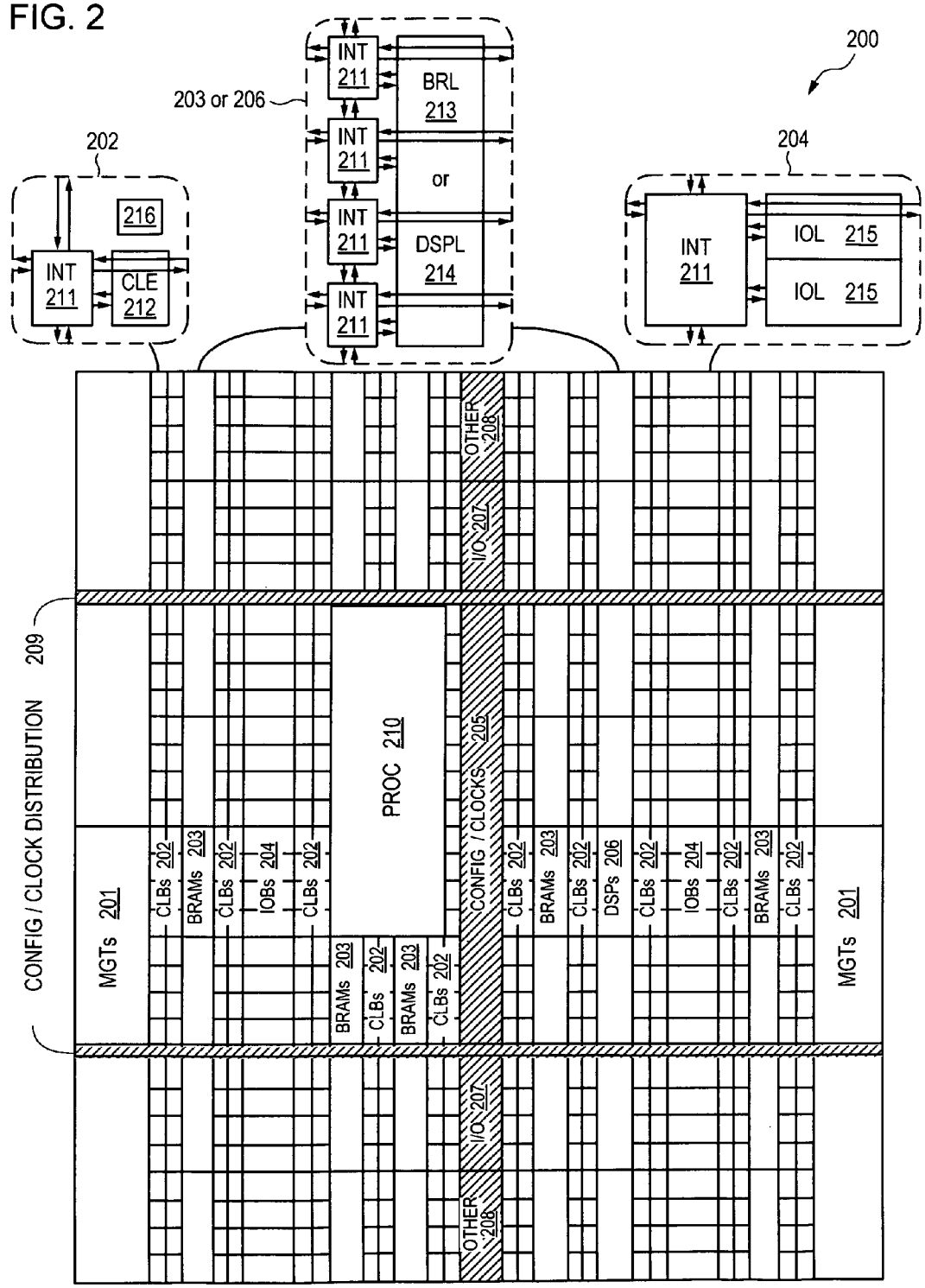

FIG. 2 is a block diagram of an example programmable logic device for which a contaminant can be identified, in accordance with various embodiments of the invention.

Advanced PLDs can include several different types of programmable logic blocks in the array. For example, FIG. 2 illustrates an FPGA architecture 200 that includes a large number of different programmable tiles including multi-gigabit transceivers (MGTs 201), configurable logic blocks (CLBs 202), random access memory blocks (BRAMs 203), input/output blocks (IOBs 204), configuration and clocking logic (CONFIG/CLOCKS 205), digital signal processing blocks (DSPs 206), specialized input/output blocks (I/O 207) (e.g., configuration ports and clock ports), and other programmable logic 208 such as digital clock managers, analog-to-digital converters, system monitoring logic, and so forth. Some FPGAs also include dedicated processor blocks (PROC 210).

In some FPGAs, each programmable tile includes a programmable interconnect element (INT 211) having standardized connections to and from a corresponding interconnect element in each adjacent tile. Therefore, the programmable interconnect elements taken together implement the programmable interconnect structure for the illustrated FPGA. The programmable interconnect element (INT 211) also includes the connections to and from the programmable logic element within the same tile, as shown by the examples included at the top of FIG. 2.

For example, a CLB 202 can include a configurable logic element (CLE 212) that can be programmed to implement user logic plus a single programmable interconnect element (INT 211). A BRAM 203 can include a BRAM logic element (BRL 213) in addition to one or more programmable interconnect elements. Typically, the number of interconnect elements included in a tile depends on the height of the tile. In the pictured embodiment, a BRAM tile has the same height as four CLBs, but other numbers (e.g., five) can also be used. A DSP tile 206 can include a DSP logic element (DSPL 214) in addition to an appropriate number of programmable interconnect elements. An IOB 204 can include, for example, two instances of an input/output logic element (IOL 215) in addition to one instance of the programmable interconnect element (INT 211). As will be clear to those of skill in the art, the actual I/O pads connected, for example, to the I/O logic element 215 are manufactured using metal layered above the various illustrated logic blocks, and typically are not confined to the area of the input/output logic element 215.

In the pictured embodiment, a columnar area near the center of the die (shown shaded in FIG. 2) is used for configuration, clock, and other control logic. Horizontal areas 209 extending from this column are used to distribute the clocks and configuration signals across the breadth of the FPGA.

The programmable interconnect and programmable logic are typically programmed by loading a stream of configuration data into internal configuration memory cells that define how the programmable elements are configured. The configuration data can be read from memory (e.g., from an external PROM) or written into the FPGA by an external device. The collective states of the individual memory cells then determine the function of the FPGA.

In one embodiment, an analyzer monitors the collective states of the configuration memory cells. The analyzer checks for corruption of the collective states from the byproducts of the radioactive decay of an isotope created by bombarding a contaminant with neutrons.

Some FPGAs utilizing the architecture illustrated in FIG. 2 include additional logic blocks that disrupt the regular columnar structure making up a large part of the FPGA. The additional logic blocks can be programmable blocks and/or dedicated logic. For example, the processor block PROC 210 shown in FIG. 2 spans several columns of CLBs and BRAMs.

Note that FIG. 2 is intended to illustrate only an exemplary FPGA architecture. The numbers of logic blocks in a column, the relative widths of the columns, the number and order of columns, the types of logic blocks included in the columns, the relative sizes of the logic blocks, and the interconnect/logic implementations included at the top of FIG. 2 are purely exemplary. For example, in an actual FPGA more than one adjacent column of CLBs is typically included wherever the CLBs appear, to facilitate the efficient implementation of user logic.

Figure 3:
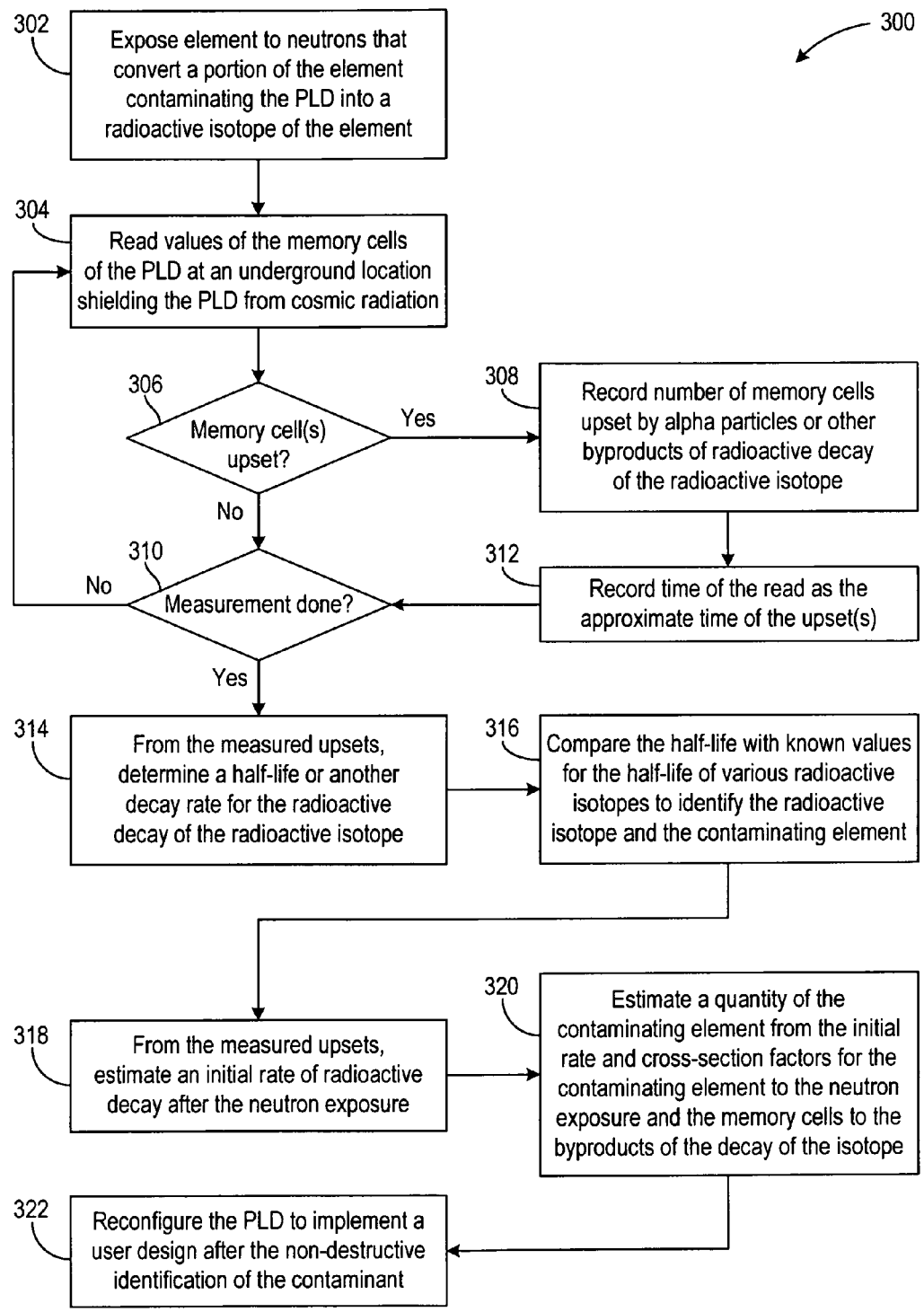

FIG. 3 is flow diagram of a process 300 for identifying an atomic element in accordance with various embodiments of the invention. The atomic element may be a contaminant that is within or nearby a programmable logic device (PLD).

At step 302, the atomic element is exposed to neutrons and these neutrons convert a portion of the atomic element into a radioactive isotope of the atomic element. It will be appreciated that the atomic element could be radioactive already; however, the half-life of the atomic element could be too long for measurement from the declining rate of upsets. The radioactive atomic element is exposed to neutron radiation to produce another radioactive isotope with a shorter and accurately measurable half-life.

At step 304, the binary states of certain memory cells of the PLD are read. In one embodiment, configuration memory cells are read at an underground location that substantially shields the PLD from cosmic radiation. Cosmic radiation produces upsets in integrated circuits and reducing the upsets from cosmic radiation permits more accurate measurement of the upsets from the radioactive isotope. An above-ground facility can expose the PLD to neutrons at step 302 and a below-ground facility can measure the upsets if the measured half-life is longer than or comparable to the time interval for transporting the PLD between the above-ground and below-ground facilities. Therefore, a below-ground location is preferred for step 304. However, in some embodiments the states of the configuration memory cells are read at an above-ground location.

Decision 306 checks whether any binary states of the memory cells are upset from expected values. If one or more memory cells are upset, process 300 proceeds to step 308; otherwise, process 300 proceeds to decision 310. At step 308, the number of upset memory cells is recorded. At step 312, the time of reading the memory cells is also recorded.

Decision 310 checks whether to continue measuring the upsets of the configuration memory cells. If the measurement is done, process 300 proceeds to step 314 to begin the analysis of the measurements. Otherwise, process 300 returns to step 304 to perform another read of the memory cells. In certain embodiments, the configuration memory cells are read continuously or periodically until there are enough measurements to determine the half-life with sufficient accuracy. In one embodiment, the declining rate of radioactive decay is accurately measurable from measurements during a time interval that is a small fraction of the half-life of the radioactive isotope. For example, measurements taken over a few days can accurately measure a half-life of 138.4 days for the radioactive isotope that is Polonium 210.

At step 314, the half-life or another rate of decay is determined from the measured upsets. In one embodiment, the measured upsets are correlated with an exponentially declining rate of decay, and the half-life for the exponentially declining rate of decay gives the half-life of the radioactive isotope. At step 316, the value of the half-life is compared with the known values of the half-lives of various radioactive elements. The radioactive isotope generated at step 302 is the radioactive element with the half-life that matches the measured half-life. The contaminating element can be identified from the radioactive isotope. In one embodiment, the exposure at step 302 changes the atomic weight of the contaminating element without changing the atomic number and the actual element, and the contaminating element is directly identified from the measured half-life. In another embodiment, the exposure at step 302 creates an unstable isotope that immediately decays into the measured radioactive isotope, and the contaminating element is a precursor of the measured radioactive isotope.

At step 318, an initial rate of radioactive decay is determined from the measured upsets. For example, the initial rate of radioactive decay is the rate of radioactive decay immediately after completing the exposure at step 302, and the initial rate is extrapolated from delayed measurements taken after transporting the PLD from a neutron generator facility to an underground measurement facility. At step 320, a quantity of the contaminating element is determined from the initial rate and two cross-sections. One cross-section is the cross-section of the contaminating element to the neutron exposure, and the other cross-section is the cross-section of the memory elements to the byproducts of the radioactive decay of the radioactive isotope.

At step 322, the PLD is reconfigured to implement a user design. An important advantage of various embodiments of the invention is that the exposure and measurement are non-destructive. After identifying the contaminant, the PLD can be configured in a normal operating mode.

The present invention is thought to be applicable to a variety of systems for identifying an atomic element within or nearby an integrated circuit. Other aspects and embodiments of the present invention will be apparent to those skilled in the art from consideration of the specification and practice of the invention disclosed herein. It is intended that the specification and illustrated embodiments be considered as examples only, with a true scope and spirit of the invention being indicated by the following claims.

What is claimed is:

1. A method for identifying an atomic element in proximity to an integrated circuit, the method comprising:
    exposing the atomic element in proximity to the integrated circuit to neutron radiation, wherein the exposing includes converting a portion of the atomic element into a radioactive isotope of the atomic element;
    measuring a plurality of upsets of binary states of a plurality of memory cells of the integrated circuit during a time period following the exposing of the atomic element to the neutron radiation; and
    identifying the atomic element from the upsets of the binary states of the memory cells of the integrated circuit.

2. The method of claim 1, wherein the atomic element is within the integrated circuit.

3. The method of claim 1, wherein the exposing the atomic element in proximity to the integrated circuit to the neutron radiation includes positioning the integrated circuit in a neutron beam.

4. The method of claim 1, wherein byproducts from radioactive decay of the radioactive isotope cause the upsets of the binary states of the memory cells.

5. The method of claim 4, wherein the byproducts are alpha particles.

6. The method of claim 1, wherein the atomic element is already radioactive with a first half-life and the radioactive isotope has a second half-life that is shorter than the first half-life.

7. The method of claim 1, wherein the measuring of the upsets of the binary states of the memory cells of the integrated circuit includes performing a sequence of reads of the binary states of the memory cells and for each read in the sequence recording a time of the read and a number of the binary states that have changed.

8. The method of claim 1, wherein the measuring of the upsets of the binary states of the memory cells of the integrated circuit includes measuring the upsets of the binary states of the memory cells which include configuration memory cells for configuring an array of programmable logic and interconnect resources of the integrated circuit which is a programmable logic device.

9. The method of claim 1, wherein the identifying of the atomic element from the upsets includes identifying the atomic element that is a contaminant within the integrated circuit.

10. The method of claim 1, wherein the identifying of the atomic element from the upsets includes determining from the upsets a rate of exponential radioactive decay of the radioactive isotope during the time period and identifying the atomic element from the rate.

11. The method of claim 1, wherein the identifying of the atomic element from the upsets includes determining a half-life of the radioactive isotope from the upsets during the time period and identifying the atomic element from the half-life.

12. The method of claim 1, wherein the identifying of the atomic element from the upsets includes estimating from the upsets an initial rate of a radioactive decay of the radioactive isotope at a beginning of the time period and estimating a quantity of the atomic element from the initial rate.

13. The method of claim 12, wherein the estimating of the quantity includes estimating the quantity of the atomic element from the initial rate and a first and second cross-section, with the first cross-section being a cross-section of the memory cells of the integrated circuit to a byproduct of the radioactive decay of the radioactive isotope, and the second cross-section being a cross-section of the atomic element to the neutron radiation.

14. The method of claim 1, further comprising using a normal function of the integrated circuit following the exposing, the measuring, and the identifying which substantially do not damage the normal function of the integrated circuit.

15. A system for identifying an atomic element, comprising:
an integrated circuit including the atomic element and a plurality of memory cells each having a binary state;
a generator of neutrons for converting a portion of the atomic element into a radioactive isotope of the atomic element, wherein a byproduct from radioactive decay of the radioactive isotope causes a plurality of upsets of the binary states of the memory cells; and
an analyzer coupled to the integrated circuit for identifying the atomic element in response to the upsets of the binary states of the memory cells.

16. The system of claim 15, wherein the integrated circuit is a programmable logic device including an array of programmable logic and interconnect resources, and the memory cells include a plurality of configuration memory cells for configuring the array to implement a user design.

17. The system of claim 15, wherein the generator generates the neutrons during a first time period and the analyzer identifies the atomic element from a half-life of the radioactive isotope determined from the upsets during a second time period following the first time period.

18. The system of claim 15, wherein the analyzer estimates an initial rate of the radioactive decay of the radioactive isotope from the upsets and estimates a quantity of the atomic element from the initial rate.

19. The system of claim 15, wherein the analyzer is coupled to the integrated circuit at an underground location for substantially eliminating additional upsets of the binary states of the memory cells from byproducts of cosmic radiation.

20. A system for identifying an atomic element in proximity to an integrated circuit, the system comprising:
means for exposing the atomic element in proximity to the integrated circuit to neutron radiation which converts a portion of the atomic element into a radioactive isotope of the atomic element;
means for measuring a plurality of upsets of binary states of a plurality of memory cells of the integrated circuit during a time period following the exposing of the atomic element to the neutron radiation; and
means for identifying the atomic element from the upsets of the binary states of the memory cells of the integrated circuit.

* * * * *